United States Patent [19]
Zhang et al.

[11] Patent Number: 5,919,479
[45] Date of Patent: Jul. 6, 1999

[54] NONINVASIVE DERMAL ANESTHETICS

[75] Inventors: Jie Zhang; Hao Zhang, both of Salt Lake City, Utah

[73] Assignee: Zars, Inc., Salt Lake City, Utah

[21] Appl. No.: 08/819,880

[22] Filed: Mar. 18, 1997

Related U.S. Application Data

[62] Division of application No. 08/508,463, Jul. 28, 1995, Pat. No. 5,658,583.

[51] Int. Cl.$^6$ ........................................................ A61F 13/00
[52] U.S. Cl. ........................... 424/449; 424/448; 514/817; 514/937; 514/938; 514/944
[58] Field of Search ................................... 424/448, 449; 514/937, 944, 938, 817

[56] References Cited

U.S. PATENT DOCUMENTS

| | | | |
|---|---|---|---|
| 3,929,131 | 12/1975 | Hardwick | 604/291 |
| 4,230,105 | 10/1980 | Harwood | 604/304 |
| 4,286,592 | 9/1981 | Chandrasekaran | 424/448 |
| 4,529,601 | 7/1985 | Broberg et al. | 514/626 |
| 4,685,911 | 8/1987 | Konno et al. | 424/450 |
| 4,693,706 | 9/1987 | Ennis, III | 604/87 |
| 4,747,841 | 5/1988 | Kuratomi et al. | 604/291 |
| 4,830,855 | 5/1989 | Stewart | 424/448 |
| 4,898,592 | 2/1990 | Latzke et al. | 604/307 |
| 4,911,707 | 3/1990 | Heiber et al. | 424/449 |
| 4,913,957 | 4/1990 | Strack et al. | 442/226 |
| 4,994,049 | 2/1991 | Latzke et al. | 604/307 |
| 5,108,710 | 4/1992 | Little et al. | 422/104 |
| 5,114,411 | 5/1992 | Haber et al. | 604/203 |
| 5,128,137 | 7/1992 | Müller | 424/449 |

(List continued on next page.)

FOREIGN PATENT DOCUMENTS

| | | |
|---|---|---|
| 2 163 956 | 3/1988 | United Kingdom . |
| 88/09169 | 12/1988 | WIPO . |

OTHER PUBLICATIONS

"Room temperature" Macmillan, U.S.A., Webster's New World College Dictionary, Third Edition, 1997, p. 1165.

Florey, Klaus "Analytical Profiles of Drug Substances", vol. 15, 1986, pp. 150–231.

(List continued on next page.)

*Primary Examiner*—D. Gabrielle Brouillette
*Attorney, Agent, or Firm*—Trask, Britt & Rossa

[57] ABSTRACT

An apparatus, product formulation, and method for improved dermal permeation of pharmaceuticals wherein the apparatus includes a thin drug formulation reservoir and a heat-generating chamber separated by a first non-permeable wall, wherein the reservoir and chamber are formed in or supported by a housing. The drug formulation reservoir houses or is capable of housing a predetermined amount of a formulation containing pharmaceutically-active agent(s). The heat-generating/temperature-regulating chamber includes a medium for generating controlled heat, preferably a chemical composition made of carbon, iron, water and/or salt which is activated upon contact with air (oxygen). The function of the heat-generating/temperature-regulating element is to heat the user's skin, rapidly bring the skin temperature to a desired and elevated narrow range and keep it in this range for sufficient time to obtain more rapid, enhanced and less variable dermal absorption of selected pharmaceutically-active agents and to obtain improved clinical effects. Structure for controlling the generation of heat is also disclosed. The apparatus may optionally include a spacing or standoff structure which spans the drug formulation reservoir between the non-permeable wall and the user's skin surface for maintaining a predetermined thickness of the drug formulation on the user's skin surface. Also, a novel product formulation which can be used with the apparatus which uses high percentage of eutectic mixture of local anesthetics to reduce the overall degradation rate of the local anesthetic compound(s) in formulations which are subject to hydrolysis.

12 Claims, 1 Drawing Sheet

U.S. PATENT DOCUMENTS

| | | | |
|---|---|---|---|
| 5,147,339 | 9/1992 | Sundström | 604/307 |
| 5,213,129 | 5/1993 | Someah et al. | 137/101.11 |
| 5,217,718 | 6/1993 | Colley et al. | 424/449 |
| 5,229,133 | 7/1993 | Wright et al. | 424/473 |
| 5,276,032 | 1/1994 | King et al. | 514/238.2 |
| 5,279,594 | 1/1994 | Jackson | 604/265 |
| 5,329,976 | 7/1994 | Haber et al. | 141/25 |
| 5,330,452 | 7/1994 | Zook | 604/307 |
| 5,364,350 | 11/1994 | Dittman | 604/89 |

OTHER PUBLICATIONS

Florey, Klaus "Analytical Profiles of Drug Substances", vol. 12, 1983, pp. 73–105.

"Local Anesthetics, Parenteral, General Statement," AHFS Drug Information, 1992.

Florey, Klaus "Analytical Profiles of Drug Substances", vol. 18, 1989, pp. 379–411.

Mack Publishing Company, "Stability of Pharmaceutical Products", *Pharmaceutical Sciences*, pp. 1481–1482, 1985.

McCafferty, et al., "Comparative *In Vivo* and *In Vitro* Assessment of the Percutaneous Absorption of Local Anaesthetics", *Br. J. Anaesth.*, vol. 60, (1988), 64–69.

Woolfson, et al., "Concentration Response Analysis of Percutaneous Local Anaesthetic Formulations", *Br. J. Anaesth.*, vol. 61, (1988), pp. 590–592.

McCafferty, et al., "*In Vivo* Assessment of Percutaneous Local Anaesthetic Preparations", *Br. J. Anaesth.*, vol. 62, (1989), pp. 18–21.

Knutson, et al., "Solvent–Mediated Alterations of the Stratum Corneum", *Journal of Controlled Release*, vol. 11, (1990), pp. 93–103.

Lycka, "EMLA, A New and Effective Topical Anesthetic", *J. Dermotol. Surg. Oncol.*, 18:859–862 (1992).

McCafferty, et al., "New Patch Delivery System for Percutaneous Local Anaesthesia", *Br. J. Anaesth.*, 71:370–374 (1993).

Sakamoto, et al., "Dermal Patch Anaesthesia: Comparison of 10% Lignocaine Gel with Absorption Promoter and EMLA Cream", *Anaesthesia*, vol. 48, (1993), pp. 390–392.

Woolfson, *Percutaneous Local Anaesthesia*, (1993), pp. 166–170.

Astra USA, Inc., "EMLA Cream Product Information Form for American Hospital Formulary Service", (1993), pp. 1–28.

NONINVASIVE DERMAL ANESTHETICS

PRIOR APPLICATION

This is a divisional of application Ser. No. 08/508,463, filed Jul. 28, 1995, now U.S. Pat. No. 5,658,583.

BACKGROUND OF THE INVENTION

1. Field of the Invention

The present invention relates to novel formulations of pharmaceutically-active agents and to novel devices and methods to obtain more rapid, enhanced and less variable dermal absorption of same, and more particularly to devices, formulations and methods for obtaining rapid, enhanced and less variable non-invasive anesthetization of the skin before painful medical procedures, such as injections, cannulations, skin grafts, biopsies, minor superficial surgeries, and the like.

2. State of the Art

The topical, dermal administration of drugs has long been known in the practice of medicine. (For purposes in this application, the terms "dermal" and "skin" relate to human skin and mucosa through or into which pharmaceutically-active agents are delivered. These pharmaceutically-active agents include but are not limited to topically, regionally, and systemically targeted drugs.) In the early 1970s, patents relating to advanced transdermal drug delivery systems began to issue. These devices were designed to hold one or more drugs and were affixed to the user such that the drug(s) contacted the user's skin for absorption of said drug(s).

In the early 1980s, more advanced systems were developed, such as U.S. Pat. No. 4,286,592 issued Sep. 1, 1981 to Chandrasekaran. This patent shows a bandage for administering drugs to a user's skin consisting of an impermeable backing layer, a drug reservoir layer composed of a drug and a carrier, and a contact adhesive layer by which the bandage is affixed to the skin.

It is known that elevated temperature can increase the absorption of drugs through the skin. It is thus conceivable that variable skin temperature can cause variable absorption of drugs in dermal drug delivery systems, which phenomenon could cause variable clinical profiles, such as variable onset time. To date, minimizing variability in skin drug absorption has been mainly through the use of rate limiting membranes, and no known prior art has attempted to minimize variability of dermal drug absorption by regulating the skin temperature. U.S. Pat. No. 4,898,592 issued Feb. 6, 1990 to Latzke et al. relates to a device for the application of heated transdermally absorbable active substances which includes a carrier impregnated with a transdermally absorbable active substance and a support. The support is a laminate made up of one or more polymeric layers and optionally includes a heat conductive element. This heat conductive element is used for distribution of the patient's body heat such that absorption of the active substance is enhanced. However, this device has no heat-generating element or function. Thus, the use of this heat conductive element to distribute body heat is not an efficient or reliable method of enhancing transdermal absorption by heating since the amount of body heat given off by a patient can vary depending on the ambient air temperature and the physical conditions of the patient.

U.S. Pat. No. 4,747,841, issued May 31, 1988 to Kuratomi et al., discloses a method and apparatus for moxibustion using a heat-generating element to heat and vaporize "moxa" for treatment of a patient's skin without leaving burn scars. Further, the focus of this patent is to achieve heat stimulation of the body and not to increase skin permeability. This teaching of heat stimulation of the body is contrary to the present invention, wherein stimulation of the body is to be minimized, particularly with pediatric patients. Finally, the reference teaches away from lower-temperature heating of the skin as not fully utilizing the moxa ingredients.

U.S. Pat. No. 4,230,105, issued Oct. 28, 1980 to Harwood, discloses a bandage with a drug and a heat-generating substance, preferably intermixed, to enhance the rate of absorption of the drug by a user's skin. Separate drug and heat-generating substance layers are also disclosed. Water must be applied to the bandage to activate the heating substance. In addition, the hydration process disclosed in this patent produces much less energy per unit mass than the heat-generating medium of the present invention. It also generates most of its heat in a relatively short time (in comparison to the medium employed in the present invention) and thus is not capable of providing stable heat for an extended duration. It is also incapable of regulating skin temperature desired range for extended duration. Once activated, heating temperature cannot be controlled.

U.S. Pat. No. 4,685,911, issued Aug. 11, 1987 to Konno et al., discloses a skin patch including a drug component, and an optional heating element for melting the drug-containing formulation if body temperature is inadequate to do so. The heating element is not substantially co-extensive with the drug reservoir, the latter being quite thick and thus not susceptible to even and rapid onset of heating.

It is desirable to noninvasively anesthetize the skin before some painful medical procedures, such as injections, cannulations, skin grafts, biopsies, minor superficial surgeries, and the like. EMLA™ (Eutectic Mixture of Local Anesthetics), a lidocaine-prilocaine formulation made by Astra, is widely used for these purposes. It is generally applied as a cream, then covered with a plastic bandage (cream-plus-cover system). EMLA's onset time (In this application, the term "onset time" is defined as the time between the start of the administration of the drug delivery system and the commencement of the desired clinical effect) in most cases ranges from about 45 to 90 minutes, or even longer, depending on the individual and the position and condition of the skin. This lengthy and quite variable onset time can cause prolonged and difficult to predict waiting on the part of patients, physicians and nurses in many situations.

EMLA's long and highly variable onset time is likely due to the two local anesthetic agents (lidocaine and prilocaine) used, as well as the lack of heating and control of skin temperature. Tetracaine is believed to be significantly better than lidocaine at producing full-depth skin anesthesia, but is subject to significant hydrolytic degradation.

A tetracaine/lidocaine eutectic mixture was discussed in U.S. Pat. No. 4,529,601 (the "'601 patent") issued Jul. 16, 1985 but not claimed.

McCafferty et al. in their publications and patents [PCT/GB88/00416; GB2163956; Br. J. Anaesth. 60:64 (1988); 61:589 (1988), 62:17 (1989), 71:370 (1993)] mentioned a number of systems and formulations for non-invasive skin anesthesia, and discussed the advantages of a patch system over a cream-plus-cover system. They stated that an effective preparation should contain the minimum concentration of local anesthetic consistent with producing the desired clinical effect, and that onset times could not be reduced further by increasing the local anesthetic concentrations in their formulations after passing certain concentration.

In addition, none of prior art systems for noninvasive skin anesthesia have element or mechanism for regulating and increasing skin temperature. The low and uncontrolled skin temperature can lead to slow and widely variable onset time of anesthetic effect. That is because skin permeabilities of drugs are generally greatly influenced by skin temperature which is affected by ambient temperature and the user's physical condition, and thus can be quite variable if uncontrolled.

Therefore, it would be advantageous to develop an apparatus and method which achieves more rapid, enhanced and less variable dermal permeation of pharmaceuticals through the means of heating the skin and regulating the skin temperature, and which, more specifically when used with anesthetics, results in shorter onset times, achieves less variation in onset times by rapidly heating the skin temperature to a desired narrow range and maintaining the temperature in this range for a desirable length of time. It would also be advantageous to develop a novel product formulation which significantly improves the shelf-life of a product that contains a pharmaceutically-active agent(s) which is subject to hydrolytic degradation.

SUMMARY OF THE INVENTION

The present invention provides some important advantages over prior art pharmaceutically-active formulations and devices for rapid, enhanced and less variable dermal drug absorption with a novel apparatus and method of using same. It also offers a novel formulation and apparatus that have important advantages over prior art formulations and apparatus for non-invasive skin anesthesia.

The present invention provides novel apparatus and formulations, and the method of using same, for achieving improved therapeutic effect by dermal absorption of phamaceutically-active agents. It also offers a method to increase relative chemical stability of certain chemically unstable ingredient(s) in the formulations.

One aspect of the present invention is a pharmaceutical administering device which has a drug formulation reservoir and a heat-generating chamber separated by a non-permeable wall, wherein the reservoir and chamber are formed in or supported by a housing, which may be formed completely or partially of a thermal insulating material to better contain the generated heat between the device and the user's skin. The drug formulation reservoir houses or is capable of housing a predetermined amount of a pharmaceutically-active formulation, preferably a firm gel under room/storage temperature which either remains as a gel, melts or significantly softens when heated, depending on the gelling agent(s) used.

The heat-generating chamber (heating element) includes means for generating controlled heat (electrical, chemical, etc.). Preferably, the heat-generating means is a chemical composition made of carbon, iron, water and/or salt which is activated upon contact with air (oxygen). The preferred heat-generating chamber has means for allowing the heat-generating medium to have limited and controlled contact with ambient air, such as a cover or housing with opening(s), areas with semipermeable membrane(s) or entire surfaces made of semipermeable membrane(s). The advantages offered by this chemical type of heat-generating composition, when used in the apparatus of this application, include high thermal energy per unit mass, rapid onset of heating, stable and controllable heating temperature over extended duration, light weight, independent operation (i.e. no need to be hooked up to any machine such as is necessary in electrical heating systems), and relatively low cost.

A typical exemplary (not necessarily optimal) heating device according to the present invention has the following values and parameters:

0.2 g heat-generating medium per $cm^2$.

heat-generating medium composition: 2:2:3 (W:W:V) activated carbon:reduced iron powder: 10% NaCl/water solution. (i.e. 2 g:2 g:3 ml)

Approximately 1.5% of the top membrane area comprises microporous polyethylene film (such as msx 1137P™, made by 3M Corp.). The rest of the top membrane areas comprises nonpermeable membrane or closed-cell foam tape.

When use under normal conditions, warmth should be felt within approximately three minutes after the device is activated. The temperature should be within 2° C. or less of the steady state temperature within ten minutes from the activation. It is possible that steady state temperature may be reached even more quickly through optimization of the heat generating medium and control mechanisms. The temperature at the skin should remain substantially at the steady state temperature (±2° C. variation) for preferably 30 minutes or longer, before cooling down slowly.

To use this pharmaceutical administering device, the user activates the heat-generating chamber (with the preferred embodiment, the user exposes the device to air by removing it from an air-tight storage container), after which the user affixes the device with the formulation containing the pharmaceutically-active agent adjacent to the skin area.

A variation of the device has very similar features as the one described above, except the drug reservoir is unloaded. To use, the user removes the device from the air-tight container to activate the heating element, places the selected drug formulation into the empty drug reservoir, then affixes the loaded device onto the skin with the drug formulation adjacent to the skin. This arrangement allows the user to use the same device with selected independent formulation to achieve improved clinical effects.

The device can also be made such that it does not have the drug reservoir, and the lower side of the bottom of the wall of the heat-generating chamber is adhesive. This device is actually an "heating cover" and can be used with selected independent transdermal drug delivery systems, such as, by way of example only, cream, gel or patch types. To use, the user removes the "heating cover" from the air-tight container, applies the independent dermal drug delivery system onto the skin, then places the "heating cover" on top of (over) the independent dermal drug delivery system. The onset time of the selected independent dermal drug delivery system as well as variations thereof may be significantly reduced by the heat generated in the heating cover. This device may potentially be used with many independent dermal drug delivery systems to achieve improved clinical effect. For example, the onset time of EMLA can be shortened by using this "heating cover," as illustrated by Example 3 herein.

The pharmaceutical administering device can also include spacing or standoff means which spans the drug formulation reservoir between the non-permeable wall and the user's skin surface. The spacing or standoff means maintains a predetermined thickness and contact surface area of the drug formulation on the user's skin surface. The spacing or standoff means, or the periphery of the housing, may include structure for engaging a gelled, solidified or viscous formulation and maintaining it in the drug formulation reservoir.

The pharmaceutical administering device of the invention effects heating the skin to a desired narrow temperature range for sufficient time to achieve rapid and less variable dermal drug absorption, and is convenient to use (i.e. light weight, small volume, not hooked up to other equipment, etc.).

Additionally, the pharmaceutical administering device, when used to administer topical anesthetics, results in a combination of shorter onset times, less variation in onset times, and greater convenience of use than presently known noninvasive topical anesthetic administering techniques.

The present invention also includes a novel anesthetic formulation which can be used with the disclosed pharmaceutical administering devices. The anesthetic formulation is an emulsion formulation, preferably a gelled-emulsion. A preferred formulation of the anesthetic is a gelled-emulsion with an oil phase being a eutectic mixture of local anesthetics (tetracaine base and lidocaine base in the preferred formulation) and an aqueous phase being water with a gelling agent(s) and/or a thickening agent(s), and optionally a pH regulating agent(s), and/or coloring agent(s). The gelled emulsion may remain as a gel, soften, or melt by body heat or external heating, depending on the gelling agent(s) and/or the thickening agent(s) used.

Compared with EMLA, the only known widely used product with similar applications, the presently claimed invention should provide shorter anesthetic onset time and less variation in onset time (see Examples 1, 3 and 4 herein), and longer duration of effect (approximately 5 to 8 hours vs. 2 hours for EMLA).

As noted above, coloring agents can also be incorporated into the formulation. The color left by the formulation on the skin can indicate the skin area treated, and thus the area which should be numb.

BRIEF DESCRIPTION OF THE DRAWINGS

While the specification concludes with claims particularly pointing out and distinctly claiming that which is regarded as the present invention, the objects and advantages of this invention may be more readily ascertained from the following description of the invention, when read in conjunction with the accompanying drawings in which:

DETAILED DESCRIPTION OF THE ILLUSTRATED EMBODIMENT

Figure 1:
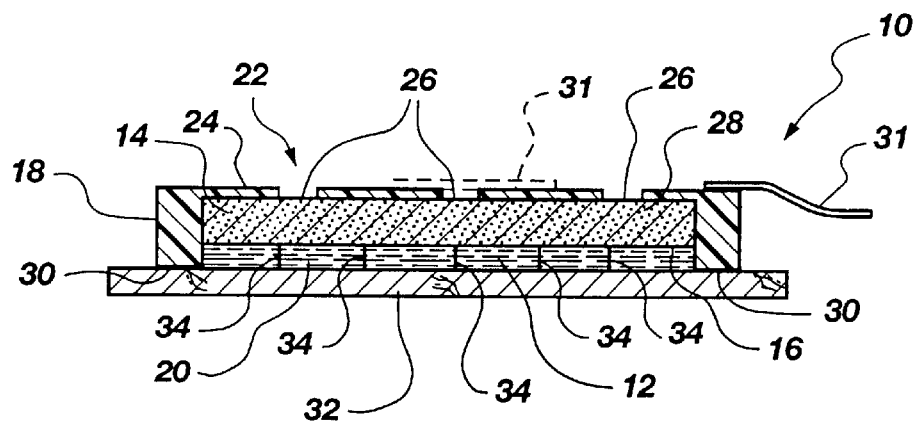
FIG. 1 is a side plan cross-sectional view of an embodiment of the pharmaceutical administering device with pre-loaded pharmaceutically-active formulation.

FIG. 1 is a side plan cross-sectional view of an embodiment of the pharmaceutical administering device 10. The device 10 has two main compartments: a drug formulation reservoir 12 and a heat-generating chamber 14 separated by a nonpermeable wall 16. The drug formulation reservoir 12 and the heat-generating chamber 14 are formed in or supported by frame or housing 18, which may be circular, rectangular, or any other suitable shape. The drug formulation reservoir 12 houses a predetermined amount of a formulation containing pharmaceutically-active agent(s) 20. Reservoir 12 and chamber 14 are preferably substantially co-extensive for uniform heating of the formulation 20 containing agents.

The heat-generating chamber 14 can utilize a variety of known means for heating (electrical, chemical, etc.). A preferred heat-generating chamber 14 comprises a heat-generating medium 28 made of carbon, iron, water and/or salt, which is activated upon contact with air (oxygen). Said preferred heat-generation chamber 14 is capped by a structure 22 which has substantially non-air permeable area(s) 24 such as area(s) preferably formed with good thermal insulating material such as closed-cell foam tapes, and opening (s) or area(s) 26 comprising material with desired permeability to air (i.e. microporous semi-permeable membranes). It is conceivable that the entire structure 22 may be made of semipermeable membrane with desired air permeability. In that case, surface 22 does not have openings or areas impermeable to air. The air (oxygen) permeation across the structure 22 may be varied to adjust the temperature and duration of the heating process.

Thus, it is necessary to store the entire preferred device 10 in an air-tight packaging, or container, or to employ a removable barrier (not shown) over the semipermeable membrane(s) or openings 26 to prevent premature activation of heat-generating medium 28.

Prior to use, the device 10 is removed from the container. The heat-generating medium 28 is activated or in the preferred embodiment begins to generate heat as air starts to flow into it through at least one opening or at least one area of semipermeable membrane 26 of surface 22. The user removes a protective bottom barrier layer (not shown) covering the drug reservoir chamber 12 to expose the formulation 20 containing pharmaceutically-active agent(s). Optionally, the housing 18 includes an adhesive surface 30 along its periphery which is simultaneously exposed with the removal of the protective bottom layer. The device 10 is then affixed to the skin area 32 to be treated, such that the formulation containing pharmaceutically-active agent(s) is adjacent the skin area 32, or optionally, the adhesive surface 30 adheres to a portion of the skin area 32 to keep the device 10 in place over the skin area 32. The housing 18 is preferably made from a flexible foam which is substantially deformable to contour to the surface of the skin area 32, thereby assuring an intimate formulation-skin contact and assisting in containing the formulation 20 within the confines of the drug formulation reservoir 12, the housing 18, and the skin area 32.

The device 10 may also include spacing or standoff means 34 between the non-permeable wall 16 and the skin area 32. The spacing or standoff means 34 may be a grid, parallel baffles, concentric circles, pins, posts, a sponge-like 3-D matrix, or any other configuration which could span or bridge the space between the first nonpermeable wall 16 and the skin area 32 while still allowing the formulation 20 to reside within the thin drug formulation reservoir 12 or within the 3-D matrix when such matrix is used. The spacing or standoff means 34 maintains the thickness of the drug formulation on the skin area 32, and prevents the drug formulation being pushed away from skin area 32 to maintain the full design surface area of contact between the formulation 20 and skin area 32.

Figure 2:
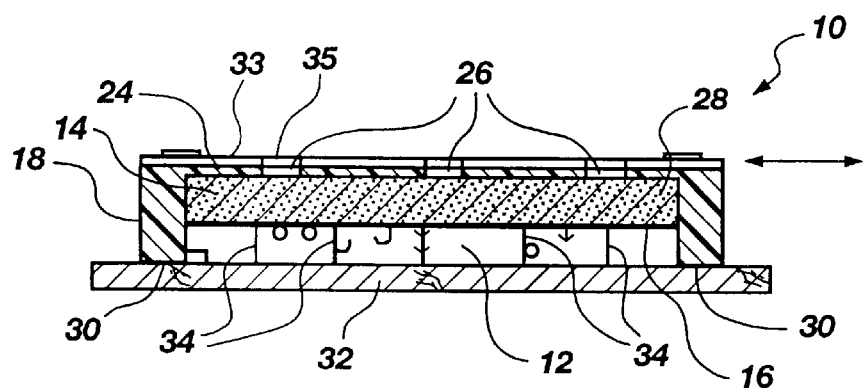
FIG. 2 is a side plan cross-sectional view of another embodiment of the pharmaceutical administering device providing an empty reservoir to be filled with a pharmaceutically-active formulation immediately before use.

It is also possible and preferable in some instances to provide formulation retention structure within or around drug formulation reservoir 12 to hold a gelled, solidified or viscous formulation 20 in the device 10 when the protective bottom layer is removed to expose the formulation 20. Such retention structure may comprise hooks, barbs or loops secured to wall 16, and which may be incorporated in spacing or standoff means 34. The housing or frame 18 may be formed with a lip or an inwardly-extending flange or inclined sidewall to engage a gelled, solidified or viscous formulation 20 at its periphery. Various structures for the aforementioned purpose are illustrated in FIG. 2 for clarity, since no formulation 20 is disposed in drug formulation reservoir 12 in that drawing figure.

It is, of course, understood that the pharmaceutical administering device 10 may be used to deliver a multitude of drugs, such as (by way of example and not limitation) antifungal agents (i.e., ciclopirox and others), antibiotics agents (i.e., mupirocin, erythromycin, and others), antiseptic agents (i.e., benzoic acid, nitrofurazone, and others), and anti-inflammatories (i.e., hydrocortisone, prednisone, and others). The drugs may be topically, regionally and systemically targeted agents (i.e., ketorolac, indomethacin and others). Additionally, penetration enhancing agents can also be incorporated. However, one preferred use is for the delivery of topical anesthetics. A preferred formulation of the anesthetic(s) is a gelled-emulsion with the oil phase being a eutectic mixture of local anesthetics (tetracaine base and lidocaine base in the preferred formulation) and the aqueous phase being water with gelling agent(s), and/or emulsifying agent(s), and, optionally, pH regulating agent (s), and/or coloring agent(s). When a coloring agent(s) is incorporated into the formulation, the color left by the formulation can indicate the skin area treated and thus the area which should be numb.

The gelled emulsion may stay as a gel or soften or melt by body heat or external heating, depending on the gelling agent(s) and/or the thickening agent(s) used.

Ingredients and their quantities in a typical exemplary (not necessarily the most optimal) formulation are as follows:
The oil phase (12% of total formulation weight):
   (1:1 W:W) tetracaine/lidocaine eutectic mixture.
The aqueous phase (88% of total formulation weight):
   5% carrageenin (gelling agent), 0.093% NaOH (pH regulating agent) in water.

Compared with much lower percentages the percentage of eutectic mixture of lidocaine and tetracaine used in the preferred formulation does not seem to provide shorter onset time. However, this novel approach, which opposes the prevailing beliefs and thinking in this art, allows a larger percentage of tetracaine base, a chemical subject to hydrolytic degradation when in contact with water, to "hide" in the eutectic mixture oil droplets and avoid contact with water. The chemical stability of overall tetracaine base in the formulation is thus dramatically improved, meaning that a smaller percentage of all tetracaine in the formulation is lost to hydrolytic degradation per unit time (see TABLES 1–3, infra). This stability improvement should make shelf-life of the formulation long enough so that it can be used in practical and commercially viable pharmaceutical products.

Other anesthetics in oily solutions or eutectic mixtures may also be used in the formulation.

Preferably, the formulation 20 containing pharmaceutically-active agent(s) (whether such agents are anesthetics or other pharmaceuticals) is a gel under room/storage temperatures which either stays as a gel or melts or softens when heated to approximately 30° C. or higher, depending on the gelling agent(s) and/or thickening agent(s) used. The gelled formulation allows easy incorporation into a patch type device which is more convenient to use than the cream-plus-cover system presently widely used in the industry. Formulations that significantly soften or melt by heating may offer more intimate contact with skin. They may also offer more sustainable and/or rapid action if the restriction of the movement of the oil phase in the formulations has significant adverse impact on the rate and/or sustainability of absorption of the active drug(s). The use of the heat-generating medium 28 in the pharmaceutical administering device 10 rapidly brings the skin temperature to desired narrow range and keep it in this range for a desired duration which significantly reduces the length and variability of onset times and increases drug flux for anesthetics as well as other pharmaceutical agents. Flux may be defined as the amount of drug across the skin per unit time per unit area in sustained release.

There are two possible mechanisms that an active drug in an oil-in-water emulsion formulation can enter the skin: first, the oil droplets contact the skin and deliver the drug to skin and second, the dissolved drug in the aqueous phase contacts and penetrates the skin. It is conceivable that while both mechanisms can exist in a given formulation, it is likely one is dominant over the other and thus determines the onset time. For emulsion formulations of the present invention, in which the oil phase is the eutectic mixture of local anesthetics, most of the active drugs exist in the oil phase. It was thus thought the first mechanism was dominant in the formulations of this invention. In situations where the first mechanism is dominant, it was believed to be crucial that the oil droplets move relatively freely in the formulation such that the drugs can keep coming to contact with the skin as the drug(s) are being absorbed by the skin. Thus, gelling the matrix was thought to have a significant adverse effect in some instances because a hydrogel is a three-dimensional polymer chain framework holding the solvent, in which movement of larger particles is more hindered than movement of smaller ones (oil droplets, even small ones, are many orders of magnitude larger than dissolved molecules). To utilize advantages of both the gel and the soft cream type matrices, it was considered in the practice of this invention most advantageous to use melting gel as the matrix of the present invention. However, it was surprisingly discovered that similar onset time is obtained in the melting type and the non-melting type gels which suggests that the onset time is determined by dermal absorption of drugs (especially tetracaine) dissolved in the aqueous phase, although that is only a small fraction of the total drug in the formulation. This surprising discovery would allow gelling the formulation, which is almost required by a patch, without compromising the onset time. Of course, it is possible that different formulations have different dominant mechanisms.

As previously mentioned, the preferred formulation uses high percentage of eutectic mixture of local anesthetics which significantly increases the chemical stability of overall local anesthetic compound(s) (such as tetracaine) which is subject to hydrolysis in water-containing formulations.

McCafferty et al. pointed out that, in their non-invasive skin anesthesia formulations, the anesthesia onset time did not shorten further with increasing percentage of local anesthetic compound (tetracaine) after certain points. The experimental results for the present invention suggest that this is true for the preferred formulation in this invention. It was observed that formulations containing approximately 6% and 12% eutectic mixture of 1:1 lidocaine base and tetracaine base provided about the same anesthesia onset time. So, given the knowledge of onset time vs. concentration relationship and drawbacks associated with high active drug concentration, a person skilled in the art would not choose to use a concentration of local anesthetics higher than this necessary concentration. However, experimental results of the inventor herein show that the use of higher eutectic mixture concentrations would significantly reduce the overall degradation rate of the hydrolysis susceptible compound(s) that is a component of the eutectic mixture, and thus prolong the shelf-life of the formulation.

The following is the analysis using an emulsion formulation, oil phase of which is the eutectic mixture of lidocaine and tetracaine (hydrolysis susceptible compound). The hydrolysis susceptible compound in such oil-in-water emulsions exist in both the oil phase (in the oil droplets) and the aqueous phase (dissolved). Only the hydrolysis susceptible compounds in the aqueous phase and at the surface of the oil droplets may undergo hydrolytic degradation, because no such reaction can take place without water (there might be trace amount of water inside the oil droplet that may cause hydrolytic degradation inside the oil droplet, but the effect should be minute). The maximum quantity of the hydrolysis susceptible compound that can exist in a given aqueous phase is limited by its aqueous solubility, which is quite low for lidocaine and tetracaine bases. Therefore, after a certain point, increasing the percentage of the eutectic mixture in the formulation does not further increase the amount of hydrolysis susceptible compound that is dissolved in the aqueous phase and subject to hydrolytic degradation (the amount of hydrolysis susceptible compound at the oil droplet surface may be slightly increased, but this effect is disproportionally small). In other words, the higher the percentage of hydrolysis susceptible compound-containing eutectic mixture in an oil/water emulsion, the lower the percentage of the total hydrolysis susceptible compound which is subject to hydrolytic degradation. The result is longer shelf life.

High percentage of local anesthetic(s) in cream-plus-over formulations may be undesirable because it increases systemic toxicity potential, especially when the formulation is not used properly (i.e. applied on a large area of compromised skin). However, the patch design of the present invention can minimize this problem by using a thin (shallow) drug reservoir as shown in the drawings, which provides a well defined contact area and allows the use of high percentage but not too high total quantities of the anesthetic agents.

This ability to increase shelf life is demonstrated by the actual experimental results below. Three formulations (A, B and C) were made. The formulations had identical aqueous phase composition (5 portions of Gelatin type B 125 bloom, 95 portions of water containing 0.4% Pemulen TR2™ (a polymeric emulsifier made by B. F. Goodrich Co.) and 0.186% NaOH), but had different concentrations of 1:1 tetracaine:lidocaine eutectic mixture: A: 6.0%, B: 12.1%, C: 2.8%. Portions of the formulations were placed in an approximately 48° C. oven with other portions at room temperature. Concentrations of tetracaine (hydrolysis susceptible compound) and lidocaine in the mixtures were determined after approximately 4 days and 55 days with high performance liquid chromatography (HPLC).

Changes in tetracaine concentrations should, and did, clearly reflect the increased stability with increasing percentage of the eutectic mixture. However, since lidocaine is much more stable than tetracaine in the aqueous environment, tetracaine/lidocaine concentration ratio in a given sample is probably a better parameter than tetracaine quantity itself to describe the stability of tetracaine, because it is much less susceptible to most of experimental errors (i.e. those from sample weighing, dilution, etc.). In other words, the higher the tetracaine/lidocaine ratio, the more stable the tetracaine. The following are experimental results:

TABLE 1

(after 4 days in 48° C. oven)

| Formulation | Eutectic mixture conc. | Average tetracaine/lidocaine ratio |
|---|---|---|
| C | 2.8% | 0.924 |
| A | 6.0% | 0.954 |
| B | 12.1% | 0.974 |

TABLE 2

(after 55 days in room temperature)

| Formulation | Eutectic mixture conc. | Average tetracaine/lidocaine ratio |
|---|---|---|
| C | 2.8% | 0.920 |
| A | 6.0% | 0.963 |
| B | 12.1% | 0.993 |

TABLE 3

(after 55 days in 48° C. oven)

| Formulation | Eutectic mixture conc. | Average tetracaine/lidocaine ratio |
|---|---|---|
| C | 2.8% | 0.102 |
| A | 6.0% | 0.375 |
| B | 12.1% | 0.671 |

The results show that over time in both room temperature and 48° C., higher content of eutectic mixture result in lower degradation rate of tetracaine in the formulation.

To obtain significantly improved overall stability of tetracaine, the preferred percentage weight of tetracaine/lidocaine eutectic mixture in the formulation is over about 6.0%, preferably over about 12.0%, and most preferably over about 18%.

An important novel feature of this invention is that the devices have the capacity to heat and regulate skin temperature to a desired and elevated, narrow range for a sufficient length of time. As mentioned above, long and highly variable onset times are two major drawbacks of EMLA, the only widely used product for noninvasive skin anesthesia. It is also known that skin permeability to pharmaceutically-active agents is significantly affected by skin temperature, which can vary widely depending the ambient temperature and the user's physical conditions. Thus, regulating skin temperature to an elevated and narrow range for sufficient time should not only shorten the onset time, but also reduce the variation in onset time and enhance flux or absorption of the pharmaceutically active agents. Both of these will benefit the patient and physician/nurse significantly. However, a device for heating/regulating skin temperature for this application is not trivia to design and make, because it has to meet several important and unique requirements: enough thermal energy in a small volume of heat-generating medium to sustain a sufficient duration of heating, rapid onset of heating balanced with desired steady state temperature, light weight, convenience of use (preferably not hooked up to an instrument), and low cost. It is also desirable to be able to vary heating temperature after activation. No known prior art device has been designed or made for this purpose or is capable of meeting all these requirements.

The preferred heating and temperature regulating element of this invention employs a chemical heat-generation composition 28 containing carbon, iron powder, water, and/or salt. The advantages offered by this heating element include high thermal energy per unit mass, rapid onset of heating, controlled and relatively stable heating temperature over extended duration, light weight, independent operation (i.e. no need to be hooked up to any machine), and low cost. Rapid onset of heating and a predetermined steady state temperature can be both achieved by selecting the quantity and composition of heat-generating medium 28 per unit area and controlling air flow rate.

It may be beneficial to optionally have a mechanism for the user to reduce and control the heating temperature. A reduction in air flow to the preferred embodiment for the heating element (i.e. activated carbon:reduced iron powder:10% NaCl/water solution) will result in a slowing of the exothermic reaction thereby reducing the heat.

One means to reduce air flow rate is to place a few small pieces of tape 30 (see FIG. 1) in a convenient place on the device. The tape can be peeled off and placed on top of the opening(s) 26, the semipermeable membrane area(s) 26 or the semipermeable membrane surface as shown in FIG. 1 in broken lines to reduce air flow and thus temperature.

Another means to reduce air flow rate is to provide the exposed area of the openings or semipermeable membrane with an adjustable (rotationally or linearly slidable) lid 32 (see FIG. 2) to close off some or all of the exposed area. Alignable apertures 34 may be included in lid 34 to effect partial closure or occlusion of multiple openings or areas 26.

A typical exemplary (not necessarily optimal) heating device, as previously referenced, has the following values and parameters:

0.2 g heat-generating medium per cm$^2$.

heat-generating medium composition: 2:2:3 (W:W:V) activated carbon:reduced iron powder:10% NaCl/water solution. (i.e. 2 g:2 g:3 ml)

1.2% of the top membrane area (area which is capable of contacting ambient air) is made of microporous polyethylene film (such as msx 1137P™ made by 3M Corp.). The remainder (i.e. 98.8% of the top membrane area) is made of nonpermeable material.

When this heat-generating medium is used as designed, the warmth should be felt within about three minutes after the device is activated. The temperature should be within 2° C. or less of the steady state temperature within ten minutes from the activation. Even shorter times may be achievable through optimization of the invention's heat generating medium and control mechanisms. The temperature at the skin should be substantially at the steady state temperature (±2° C. variation) for a duration of preferably 30 minutes or longer, before cooling down slowly.

FIG. 2 is a side plan cross-sectional view of another embodiment of the pharmaceutical administering device 10. The embodiment shown in FIG. 2 is very similar to the embodiment shown in FIG. 1, therefore the drawing numbers for similar elements are the same. The embodiment shown in FIG. 2 does not include the formulation 20 containing a pharmaceutically-active agent in the initial structure of device 10. Rather, a drug formulation is placed into the thin drug formulation reservoir 12 immediately before application of device 10 to the skin of the patient. The device 10 shown in FIG. 2 has an empty drug formulation reservoir 12 to accommodate the drug formulation and a heat-generating chamber 14, the two compartments being separated by a non-permeable wall 16 supported by the housing 18. The heat-generating chamber 14 includes at least one surface 22 comprising a non-permeable membrane 24 having means for contacting ambient air such as at least one opening 26 or at least one area of semipermeable membrane 26, or an entire surface of semipermeable membrane with desired air permeability, as described above for FIG. 1. The device 10 may also include spacing or standoff means 34 between the first non-permeable wall 16 and the skin area 32, as described above with respect to FIG. 1.

The device 10 is stored in an air-tight container (not shown). Prior to use, the device 10 is removed from the container and the drug formulation is placed into the drug formulation reservoir 12 of the device 10. The device 10 is then applied onto the skin area 32 to be treated.

Figure 3:
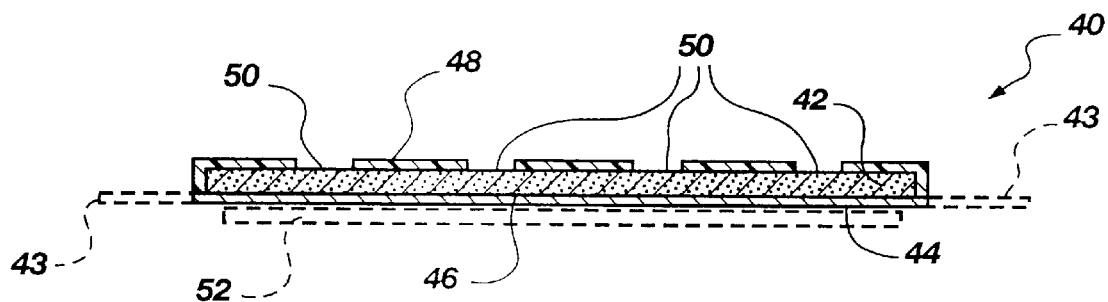
FIG. 3 is a side plan cross-sectional view of yet another embodiment of the pharmaceutical administering device which omits a reservoir and is placed over an independent dermal drug deliver system which is first applied to the skin.

The present invention can also be structured without the drug reservoir, as shown in FIG. 3. It is thus a tape 40 with a heat-generating chamber 42 on the top ("heating cover"). The tape may be fabricated of similar materials to the structures of FIGS. 1 and 2. The lower side 44 of the heat-generating chamber wall 46 contacting the skin is preferably adhesive, or an adhesive skirt 43 (shown in broken lines) may be formed around the periphery of the heat-generating chamber 42. As in the other embodiments, the upper wall 48 of heat generating chamber 42 may be provided with openings or semipermeable membrane areas 50, or may be completely formed of a semipermeable membrane. Tape or lid-type temperature regulating elements may also be provided. This "heating cover" may be placed on top of various types (i.e. creams, patches, ointments) of independent dermal drug delivery systems (shown generally in broken lines as 52) to elevate and regulate the skin temperature for achieving improved clinical effects.

It should be appreciated that the heating cover embodiment of FIG. 3 differs from prior art devices within the knowledge of the inventors in that no prior art device is formed as a free-standing (e.g., independent) heating element for the promotion of dermal drug delivery, or is to be used with other, separate and independent dermal drug delivery systems, such as the aforementioned cream, patch or ointments types. Further, none of the known prior art can achieve a combination of rapid onset time of heating, steady state temperature within a range suitable for drug delivery, sufficient duration of steady-state heating, and light weight.

EXAMPLE 1

I. The Manufacturing of an Exemplary Prototype

1. The Formulation

Liquid #1 (aqueous phase): Five portions (weight) of Gelatin (type B, 250 bloom) was added into 95 portions (weight) of a solution made of 0.4% Pemulen TR2™ (B. F. Goodrich Co.), 0.186% NaOH and the balance of water. The mixture was heated and stirred until the Gelatin was dissolved. Air bubbles were removed by centrifugation. Four and eight hundredths grams of this solution was placed into a disposable syringe.

Liquid #2 (oil phase): Equal weights of tetracaine base and lidocaine base were placed into a glass vial. The mixture was heated to approximately 60° C. and shaken until a homogeneous liquid was obtained, then cooled to room temperature. The mixture (eutectic mixture of lidocaine and tetracaine) stayed as liquid at room temperature. One and four hundredths of a gram of this liquid was placed into a second disposable syringe.

The two syringes were connected with a 3-way stopcock, and the contents of the syringes were pushed back and forth 60 times to obtain a white emulsion. The emulsion stayed as a flowable and viscous liquid when temperature was higher than approximately 30° C., but solidified when the temperature was significantly cooler.

2. The Drug Reservoir in the Patch

A ring of foam tape (inside diameter $^{15}/_{16}$ inch, outside diameter $1^3/_8$ inch, thickness $^1/_{32}$ inch, foam tape 9773, 3M Corp.) was cut from the foam tape sheet and placed on a release liner disc with a diameter of 1⅜ inch, so a 1/32 inch tall, 15/16 inch diameter drug reservoir was formed. The formulation was injected into the reservoir while still liquid. The top of the reservoir was covered with a disk of a polymer tape. The formulation became a gel after cooling down.

3. The Heat-generating Chamber

A ring of foam tape as discussed in step 2 was obtained, and placed on top of the drug reservoir made in step 2. This formed a heat-generating chamber.

In a glass vial, 1.5 g activated carbon, 2.1 g reduced iron powder and 2.1 ml 10% NaCl were placed into a glass vial and mixed thoroughly. The vial was tightly capped. This was the heat-generating medium.

A 1⅜ inch diameter disk was cut from the 1/32 inch thick foam tape. Three holes were punched on the foam tape, each having a diameter of 0.15 cm, each about 0.6 cm from the center of the disk, and 120° apart from each other. A 15/16 inch disk was cut from a microporous polyethylene film (such as msx 1137P, 3M Corp.), and placed on the adhesive side of the foam tape disk with holes. This was the heat-generating chamber cover.

Approximately 0.4 g heat-generating medium was placed into the heat-generating reservoir before the heat-generating chamber cover was placed on top of the heat-generating reservoir.

4. Storage Container of the Device

The device made above was placed into an air-tight container immediately after it was made. The container's opening was then sealed with a bag sealer.

It should be noted that it is possible, by making the heat-generating chamber deeper and placing more heat-generating medium into the chamber, as well as by optimizing the air flow rate for a particular application, that the function of-the device described immediately above might be further improved.

II. Use and Effect of the Device in Comparison to EMLA

EMLA was squeezed out from the container onto the dorsum of the right hand of a human subject (one of the inventors herein) and covered with a plastic tape. The device of the invention made as described immediately above was taken out of the storage container. The release liner at the bottom of the drug reservoir was peeled off before the device was affixed on the dorsum of the left hand of the human subject. At predetermined intervals, the skin areas being treated were pricked with a blunt needle and the pain sensation was recorded. The effect scores were defined as follows:

0: no effect
1: between no numbness and medium numb
2: medium numb
3: almost completely numb
4: completely numb, but not deep
5: completely numb and deep.

The results were, as follows:

| Time from Application | EMLA effect score | Device effect score |
|---|---|---|
| 20 min | 0 | 5 |
| 25 min | 0 | 5 (device removed) |
| 30 min | 0 | 5 |
| 35 min | 1 | 5 |
| 40 min | 1–3 | 5 |
| 45 min | 4–5 | 5 |
| 50 min | 5 | 5 |

This result clearly suggests that the onset time of the device of the invention is significantly shorter than that of EMLA.

EXAMPLE 2

One potential manufacturing procedure for an exemplary sample formulation is as follows:

Step 1:

Heat and stir 1:1 (weight) ratio of tetracaine base: lidocaine base to above 60° C., until a homogeneous liquid is obtained, then let the liquid cool to room temperature. This is the oil phase.

Step 2:

Add selected gelling agent(s) [i.e. carrageenin, gelatin] into water. Heat water to a temperature higher than the melting point of the gel to be made [i.e.—higher than 35° C. for gelatin, higher than 70° C. for carrageenin or carrageenin/gelatin combination]. Stir to make homogeneous solution. Centrifuge to eliminate air bubbles. This is the aqueous phase.

Step 3:

Emulsify the oil and aqueous phases (weight ratio 5:95 to 50:50, preferably 8:92–30:70, most preferably 12:88–24:76) while the aqueous phase is still warm enough to be a liquid. Keep this emulsified liquid (a viscous white fluid) in a temperature higher than its melting point until it is injected into drug reservoirs of devices. The maximum time between the start of emulsifying process and the injection is 24 hours, preferably 6 hours, and most preferably 1 hour (to minimize hydrolytic degradation of tetracaine which has a high rate at elevated temperatures).

Step 4:

Inject the formulation into the drug reservoirs while the formulation is warm enough to stay as a liquid, then cool to obtain gel.

EXAMPLE 3

EMLA was squeezed out of the container onto two areas of the skin of the left thigh of a human subject (one of the inventors herein). The two selected areas each had an area of approximately 4 cm$^2$ and their centers were approximately 4 cm apart. After applying EMLA, one of the areas was covered with a plastic tape, the other with an activated heating element similar to the heating chamber described in EXAMPLE 1, comprising a heating cover as described with respect to FIG. 3. At a comparable position of the right thigh, a device with formulation and heating element similar to that described in EXAMPLE 1 was applied. The pain sensation and the effective score were measured in a similar way as that previously described in Section II of EXAMPLE 1. The results were as follows:

| Time | EMLA without heating | EMLA with heating | Invention (with heating) |
|---|---|---|---|
| 15 | 0 | 0 | 4.5 |
| 20 | 0 | 0 | 4–4.5 |
| 25 | 0 | 0 | 4–5 (device removed) |
| 30 | 0 | 1–2 | 5 |
| 35 | 0 | 1–2.5 (heating element and cream removed) | 5 |
| 40 | 1 | 4–4.5 | |
| 50 | 0–1 (cream removed) | 4.5–5 | |
| 60 | 4 | 5 | |

These results suggest two things:

1. The system of this invention has a shorter onset time than EMLA even if EMLA is used with the heating element ("heating cover"). This is believed to be due to the superior formulation of the invention.

2. Heated EMLA resulted in shorter onset time than unheated EMLA. This demonstrates the effect of the "heating cover" (FIG. 3) when used with independent dermal drug delivery system.

EXAMPLE 4

The position of the EMLA application and placement of the device of the invention is on the lower legs of the subject, one of the inventors herein.

| Time | EMLA (without heating) | Invention (with heating) |
|---|---|---|
| 15 | 0 | 0 |
| 20 | 0 | 2 |
| 25 | 0 | 2–3 |
| 30 | 0 | 4–4.5 (device removed) |
| 35 | 0 | 4.5 |
| 40 | 0 | 5 |
| 45 | 0 | 5 |
| 50 | 0 | |
| 60 | 0 | |
| 70 | 0 | |
| 80 | 1 | |
| 90 | 1–3 | |
| 100 | 2 (EMLA removed) | |
| 114 | 4–4.5 | |

These results, along with that in Examples 1 and 3, suggest that the current invention provides not only shorter onset times, but also less variation in onset times. It should also be pointed out that the devices used in these examples were not thought to be finally optimized or manufactured under tight quality control as they might be in commercial production. Optimization of the system, especially the heating element, are expected to provide even better results. The heating lasted ten to fifteen minutes. The skin of the subject was quite cold at inception of heating.

EXAMPLE 5

An example of another heating medium composition is activated carbon and iron powder in a 1:1 W:W ratio. To 56 portions of the C:Fe powder (by weight), 42 portions of 10% NaCl in water is added (by volume). For example, 5.6 g of 1:1 C:Fe powder is mixed thoroughly with 4.2 ml 10% NaCl in water to obtain loose granules. The granules may be frozen, then placed in an appropriate housing. When activated, the heat generated by this formulation in a housing was measured with a thermocouple placed between the heating device and a foam tape. Within three minutes of activation, a temperature of 29° C. was observed, and within about ten minutes, a relatively stable temperature of 37° C. was attained, which was then maintained for about fifty minutes, when the thermocouple was removed.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A formulation with reduced degradation rate of anesthetic(s) and improved noninvasive dermal anesthesia comprising:

an emulsion with an oil phase and an aqueous phase; and said oil phase being a eutectic mixture of tetracaine and lidocaine, wherein the weight percentage of said eutectic mixture in said formulation is about 12% or greater.

2. The formulation of claim 1, wherein said emulsion is thickened such that it is substantially non-flowable and cohesive at ambient temperature.

3. The formulation of claim 1, further including pH regulating agent(s), coloring agent(s), permeation enhancing agent(s), or a combination thereof.

4. The formulation of claim 1, wherein the ratio of tetracaine to lidocaine is between 1:0.5 and 1:1.5.

5. The formulation of claim 1, wherein said tetracaine and lidocaine in said eutectic mixture is formulated in a substantially one to one weight ratio.

6. The formulation of claim 1, wherein the weight percentage of said eutectic mixture in said formulation is greater than about 18%.

7. The formulation of claim 1, further including at least one compound that is an emulsifying agent, a gelling agent, or a thickening agent.

8. The formulation of claim 7, wherein said emulsion is gelled.

9. The formulation of claim 8, wherein said gelled emulsion rapidly melts or significantly softens when heated to greater than about 30° C.

10. The formulation of claim 8, wherein said gelled emulsion does not melt or significantly soften when heated to about 30° C.

11. A formulation with reduced degradation rate of anesthetic(s) and improved noninvasive dermal anesthesia comprising:

a gelled-emulsion with an oil phase and an aqueous phase which melts or significantly softens when heated to about 30° C.;

said oil phase being a eutectic mixture of tetracaine and lidocaine;

the weight percentage of said eutectic mixture in said emulsion being about 12% or greater;

said formulation having at least one compound that is an emulsifying agent, a gelling agent, or a thickening agent; and said gelled-emulsion optionally including pH regulating agent(s), coloring agent(s), permeation enhancing agent(s), or a combination thereof.

12. A formulation with reduced degradation rate of anesthetic(s) and improved noninvasive dermal anesthesia comprising:

a gelled-emulsion with an oil phase and an aqueous phase which does not melt or significantly softens when heated to about 30° C.;

said oil phase being a eutectic mixture of tetracaine and lidocaine;

the weight percentage of said eutectic mixture in said emulsion being about 12% or greater;

said formulation having at least one compound that is an emulsifying agent, a gelling agent, or a thickening agent; and said gelled-emulsion optionally including pH regulating agent(s), coloring agent(s), permeation enhancing agent(s), or a combination thereof.

* * * * *